(12) United States Patent
Maguire et al.

(10) Patent No.: US 10,470,773 B2
(45) Date of Patent: Nov. 12, 2019

(54) VESSEL OCCLUDER

(71) Applicant: Terumo Corporation, Tokyo OT (JP)

(72) Inventors: Shannon Maguire, Huntington Beach, CA (US); Jessica Liang, Irvine, CA (US); Wendy Graczyk Beuthin, San Clemente, CA (US); Tin Luong-Uhl, Huntington Beach, CA (US); Peter Soliman, Rancho Santa Margarita, CA (US)

(73) Assignee: Terumo Corporation, Tokyo (JP)

( * ) Notice: Subject to any disclaimer, the term of this patent is extended or adjusted under 35 U.S.C. 154(b) by 135 days.

(21) Appl. No.: 15/619,296

(22) Filed: Jun. 9, 2017

(65) Prior Publication Data

US 2017/0354421 A1    Dec. 14, 2017

Related U.S. Application Data

(60) Provisional application No. 62/348,729, filed on Jun. 10, 2016.

(51) Int. Cl.
    *A61B 17/12* (2006.01)
    *A61B 17/00* (2006.01)
    *A61B 90/00* (2016.01)

(52) U.S. Cl.
    CPC .... *A61B 17/12159* (2013.01); *A61B 17/0057* (2013.01); *A61B 17/1214* (2013.01); *A61B 17/12109* (2013.01); *A61B 17/12172* (2013.01); *A61B 17/12177* (2013.01); *A61B 2017/00575* (2013.01); *A61B 2017/00592* (2013.01); *A61B 2017/00597* (2013.01); *A61B 2017/00623* (2013.01); *A61B 2017/1209* (2013.01); *A61B 2017/12068* (2013.01); *A61B 2090/3966* (2016.02)

(58) Field of Classification Search
    CPC ........ A61B 17/12022; A61B 17/12159; A61B 17/12109; A61B 17/1214; A61B 17/12145; A61B 17/1215; A61B 17/12168; A61B 17/12172; A61B 17/12177; A61B 2017/00597
    See application file for complete search history.

(56) References Cited

U.S. PATENT DOCUMENTS

| 5,925,060 A | 7/1999 | Forber |
| 6,120,534 A * | 9/2000 | Ruiz ................ A61B 17/12109 606/194 |
| 6,221,086 B1 | 4/2001 | Forber |
| 6,428,558 B1 | 8/2002 | Jones et al. |

(Continued)

FOREIGN PATENT DOCUMENTS

WO    WO2015/095538 A1    6/2015

OTHER PUBLICATIONS

WIPO, U.S. International Search Authority, International Search Report and Written Opinion dated Aug. 14, 2017 in International Patent Application No. PCT/US2017/036872, 8 pages.

*Primary Examiner* — Katherine M Rodjom
(74) *Attorney, Agent, or Firm* — Inskeep IP Group, Inc.

(57) ABSTRACT

A vessel occluder used to occlude blood flow within the vasculature is described. The vessel occluder can include an expandable mesh portion having a flexible membrane that expands within a cavity of the expandable mesh portion. When expanded, the flexible membrane blocks blood passage through the mesh portion.

18 Claims, 10 Drawing Sheets

(56) References Cited

U.S. PATENT DOCUMENTS

| | | |
|---|---|---|
| 6,554,849 B1 | 4/2003 | Jones et al. |
| 6,589,256 B2 | 7/2003 | Forber |
| 6,592,617 B2 | 7/2003 | Thompson |
| 6,638,257 B2 | 10/2003 | Amplatz |
| 7,001,409 B2 | 2/2006 | Amplatz |
| 7,306,622 B2 | 12/2007 | Jones et al. |
| 7,771,452 B2 | 8/2010 | Pal et al. |
| 8,043,326 B2 | 10/2011 | Hancock et al. |
| 8,308,752 B2 | 11/2012 | Tekulve |
| 8,313,505 B2 | 11/2012 | Amplatz et al. |
| 8,498,670 B2 | 3/2013 | Amplatz et al. |
| 8,641,777 B2 | 2/2014 | Strauss et al. |
| 8,747,453 B2 | 6/2014 | Amplatz et al. |
| 8,747,597 B2 | 6/2014 | Rosqueta et al. |
| 8,777,974 B2 | 7/2014 | Amplatz et al. |
| 9,039,724 B2 | 5/2015 | Amplatz et al. |
| 9,095,342 B2 | 8/2015 | Becking et al. |
| 2001/0012949 A1 | 8/2001 | Forber |
| 2007/0288040 A1 | 12/2007 | Ferree |
| 2008/0183203 A1 | 7/2008 | Fitzgerald et al. |
| 2008/0281350 A1 | 11/2008 | Sepetka et al. |
| 2009/0082803 A1 | 3/2009 | Adams et al. |
| 2010/0030256 A1 | 2/2010 | Dubrul et al. |
| 2011/0152993 A1* | 6/2011 | Marchand ........ A61B 17/12022 623/1.2 |
| 2011/0224776 A1 | 9/2011 | Sepetka et al. |
| 2011/0319926 A1* | 12/2011 | Becking ........... A61B 17/12022 606/200 |
| 2014/0200607 A1 | 7/2014 | Sepetka et al. |
| 2014/0364899 A1 | 12/2014 | Ginn et al. |
| 2015/0289879 A1 | 10/2015 | Bowman |
| 2015/0366649 A1* | 12/2015 | Tafti .................... A61F 2/01 606/200 |

\* cited by examiner

VESSEL OCCLUDER

RELATED APPLICATIONS

This application claims priority to U.S. Provisional Application Ser. No. 62/348,729 filed Jun. 10, 2016 entitled Vessel Occluder, which is hereby incorporated herein by reference in its entirety.

BACKGROUND OF THE INVENTION

Vessel occlusion may be desirable for a number of reasons. Circumstances include treatment of aneurysms, left atrial appendage, atrial septal defect, fistulas, patent foramen ovale, patent ductus arteriosus, vessel shutdown, or various occlusive purposes in the neuro-vasculature and peripheral vasculature.

Embolic coils are often used for occlusive purposes. The coils fill the target treatment site, but may require a substantial amount of time to occlude the treatment area. Vessel plugs conform to the malformation, vessel, or target treatment area and can provide a rapid occlusive effect. Vessel plugs are often used where rapid occlusion is desired, since the vessel plug can quickly fill and conform to the target space. Vessel plugs, in order to be effective, typically should be easily deployable, promote rapid occlusion, and resist migration after deployment. However, conventional vessel plugs rarely excel at all of these factors.

SUMMARY OF THE INVENTION

The present invention is generally directed to a vascular plug.

In one embodiment, the vascular plug comprises a braided mesh portion that expands from a generally linear configuration to a three-dimensional shape. For example, the mesh portion can expand to a generally spherical shape, a concave shape, a flattened oval shape, or a plurality of connected bulbs.

The vascular plug may include a flexible membrane deployed within an interior of the mesh portion when expanded. For example, the flexible membrane can comprise a circular, flat membrane arranged substantially perpendicular to a linear axis of the vascular plug. In another example, the flexible membrane expands to a position that is non-perpendicular to the axis of the vascular plug.

In one embodiment, the flexible membrane is composed of PET, ePTFE, or a thin metallic film.

In one embodiment, the vascular plug and its attached pusher are configured to delivery microcoils or other embolic material within the mesh portion or outside of the mesh portion.

In one embodiment, the vascular plug includes an elastic member within the mesh portion to assist in expansion of the vascular plug within a patient.

The present invention is also directed to a method of deploying a vascular plug within a patient.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
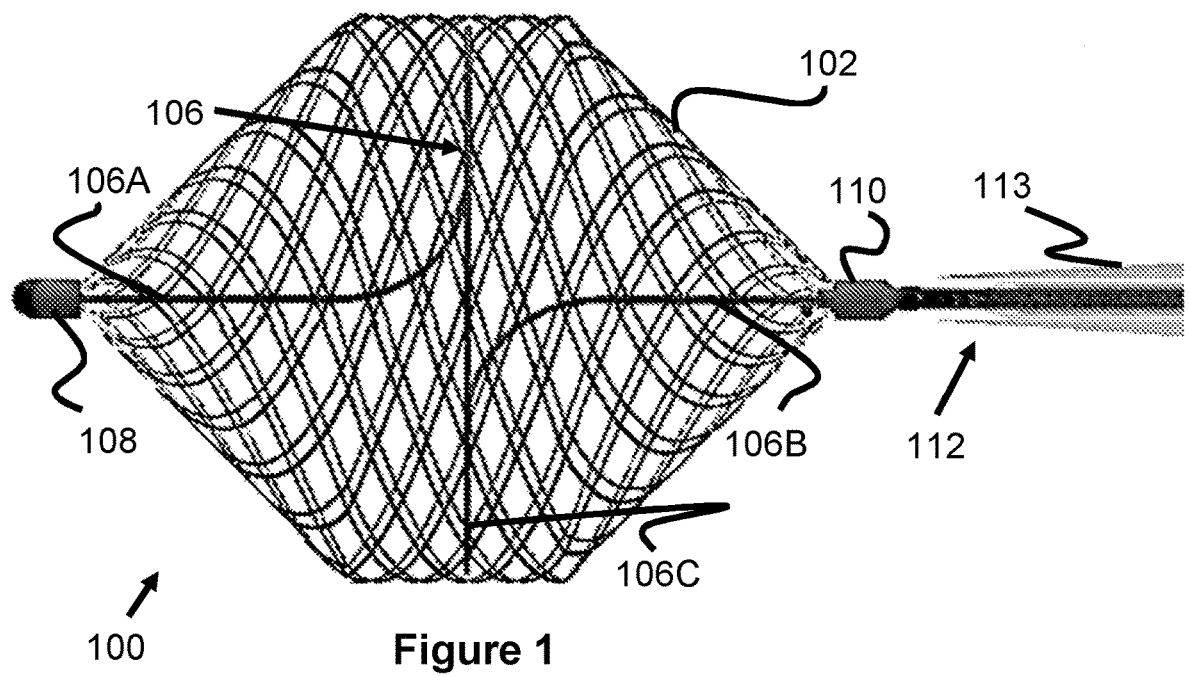
FIG. 1 illustrates a vascular plug according to the present invention.
Figure 2:
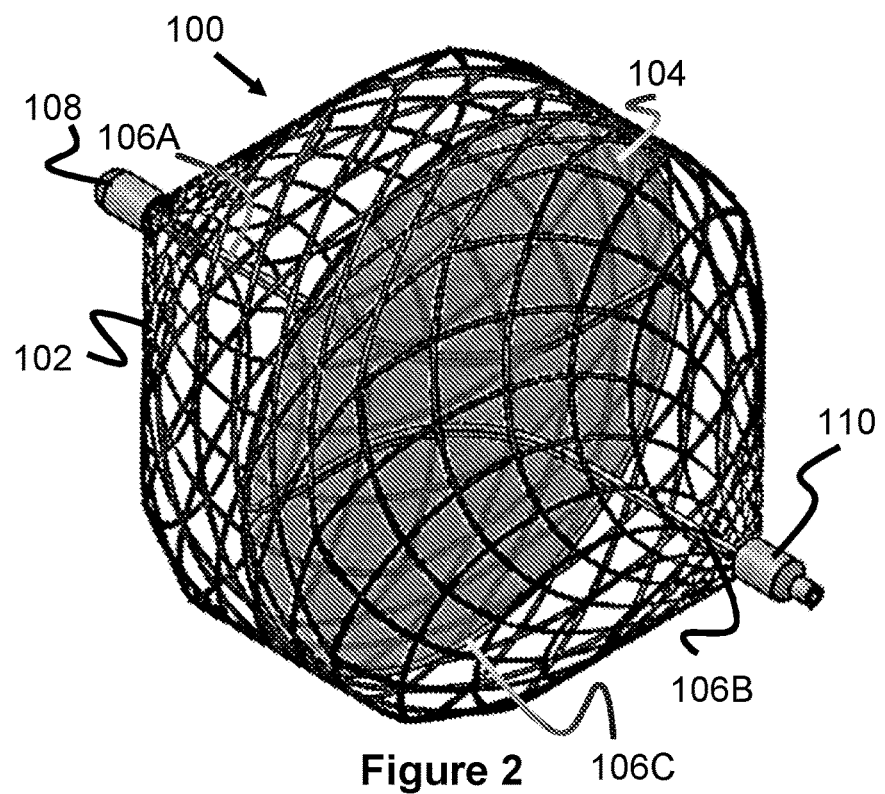
FIG. 2 illustrates a vascular plug according to the present invention.
Figure 3:
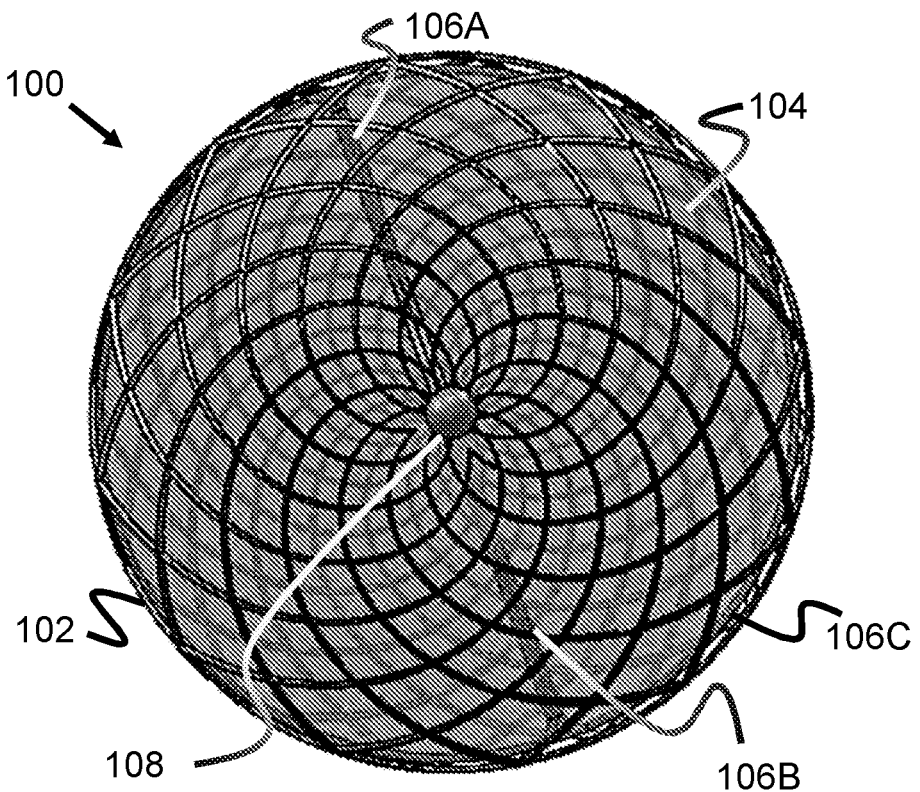
FIG. 3 illustrates a vascular plug according to the present invention.
Figure 4:
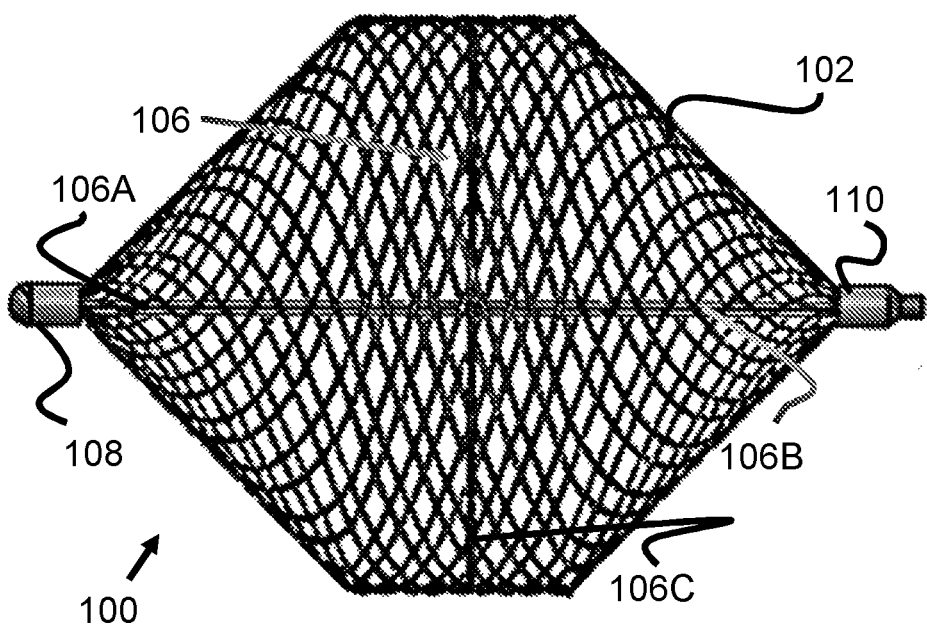
FIG. 4 illustrates a vascular plug according to the present invention.
Figure 5:
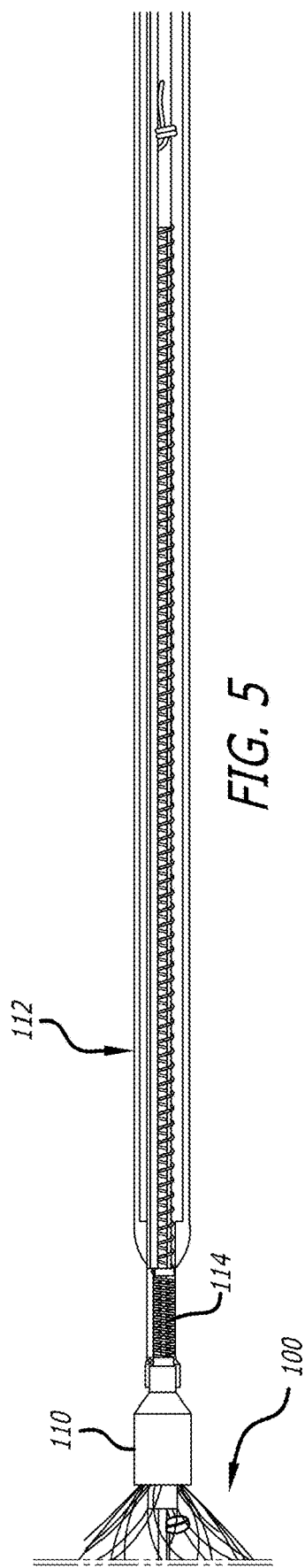
FIG. 5 illustrates a pusher and detachment mechanism.
Figure 6:
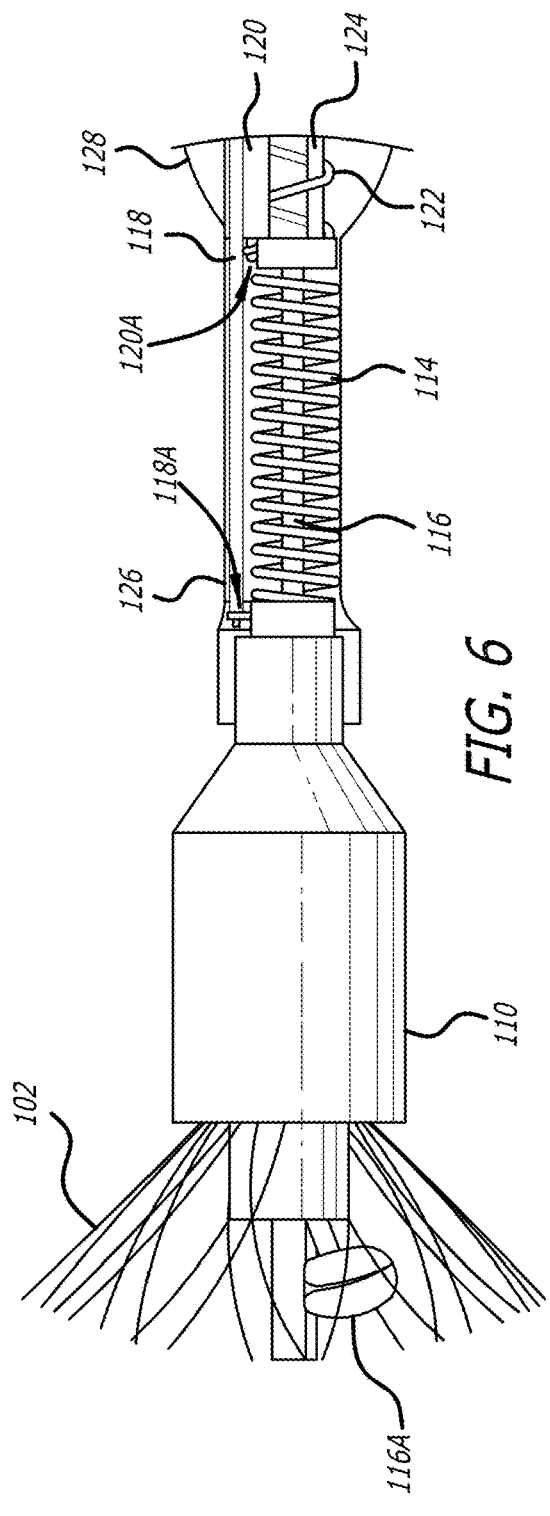
FIG. 6 illustrates a pusher and detachment mechanism.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Vascular plugs are used for various occlusive purposes in the vasculature. These plugs generally conform to the shape of the blood vessel or blood vessel abnormality thereby occluding and preventing blood flow through or to the target area. Plugs can be used to treat a variety of conditions including aneurysms, left atrial appendage, atrial septal defect, fistulas, patent foramen ovale, patent ductus arteriosus, vessel shutdown, or can be used for various occlusive purposes in the neuro-vasculature and peripheral vasculature.

Plugs generally provide faster occlusion than other occlusive devices such as embolic coils since, rather than filling the target space, the plugs conform to the shape of the target space promoting faster occlusion. Vascular plugs generally are larger than other occlusive devices (such as embolic coils) since they are meant to conform to the target space, rather than fill the target space. This larger profile can make deliverability an issue as compared to other occlusive devices, therefore, vascular plugs need to balance the need for rapid occlusion with the need for ease of deliverability in order to effectively deliver the plug to the target treatment site.

FIGS. 1-8 illustrate various aspects of a vascular plug 100 that is connected to a distal end of a pusher 112, allowing the plug 100 to be advanced through a catheter 113 to a desired target location in a patient. When a mesh portion 102 of the vascular plug 100 is expanded, a flexible membrane 104 is also expanded within the mesh portion 102 to create a blockage or barrier at the target location.

The mesh portion 102 expands from an elongated, compressed, cylindrical shape (e.g., when located within the catheter 113) to a longitudinally shorter and generally spherical expanded shape. The wires of the mesh portion 102 can be formed from nitinol, cobalt-chromium, stainless steel wires, or combinations therein. In one example, the mesh portion 102 is comprised of 48-144 nitinol wires with a diameter range of about 0.0008"-0.005". Optionally, one or more radiopaque wires can be used to create the mesh portion 102, to further enhance visualization of the vascular plug 100 during a procedure.

The distal end of the mesh portion 102 terminates with a distal cap member 108 and the proximal end of the mesh portion 102 terminates with a proximal cap member 110. These cap members 108 and 110 can be formed by welding the wires of the mesh portion together, welding the wires to discrete metal caps, crimping metal cap members onto the wires, or using an adhesive to attach discrete caps to the wires. Preferably, these cap members 108 and 110 can be composed of radiopaque materials such that they can be used as visual markers during a procedure.

The flexible membrane 104 is described as a membrane, but can be any material that can be unfolded, straightened, stretched, or otherwise expanded to an enlarged and preferably planar area. The flexible membrane 104 can be composed of a variety of flexible materials that are biocompatible and preferably that increase a thrombogenic response in the patient. For example, polyethylene terephthalate (PET) or expanded polytetrafluoroethylene (ePTFE) can be used. In another specific example, a composite of PET and ePTFE can be used. In another example, the flexible membrane 104 can be composed of a thin-metallic film, such as those created via sputtering or vacuum deposition.

The flexible membrane 104 is supported by support frame 106, located within the cavity of the mesh portion 102. The support frame 106 includes a circular ring portion 106C that expands to a diameter that is similar in size to the largest inner diameter region of the expanded mesh portion 102 and is oriented such that the plane of the ring portion 106C is generally perpendicular to an axis between the proximal and distal end of the mesh portion (e.g., an axis between the caps 108 and 110). This orientation allows the flexible membrane 104 to be expanded almost completely across the cavity of the mesh portion 102 and block passage of fluid from a patient between the proximal and distal ends of the vascular plug 100.

The flexible membrane 104 can be fixed to the ring portion 106C by creating a laminating layer over the flexible membrane 104, around the wire of the ring portion 106C, and back upon itself. For example, the flexible membrane 104 can be initially created with PET and a layer of ePTFE can be disposed or laminated over the PET layer and the ring portion 106C. Alternately, the flexible membrane 104 can be stitched to the ring portion 106C with metal wires or polymer fibers. In another alternate embodiment, adhesives can be used for attachment purposes. In yet another alternate embodiment, the flexible membrane 104 can be directly stitched or adhered to the wires of the mesh portion 102.

The ring portion 106C is preferably supported by a distal support arm 106A and a proximal support arm 106B. The distal support arm 106A is connected at its distal end to the distal cap member 108 and extends axially, curving radially outward near a center of the mesh portion 102, and ultimately connecting to the ring portion 106C. Similarly, the proximal support arm 106B is connected at its proximal end to the proximal cap member 108 and extends axially, curving radially outward near a center of the mesh portion 102, and ultimately connecting to the ring portion 106C. The distal support arm 106A may connect to the ring portion 106C at a diametrically opposite location to the connection point of the proximal support arm 106B. In other embodiments, multiple support arms can be connected in a similar manner to the ring portion 106C. For example, 2, 3, 4, or 5 can be included on both the proximal and distal sides of the ring portion 106C.

As seen in FIGS. 5-8, the vascular plug 100 can be detached from the pusher 112 via a heater coil 114 on the distal end of the pusher 112 that breaks a tether filament 116. Specifically, the tether filament 116 is connected to the pusher 112 (e.g., to a structural coil 122), passes through the interior of the heater coil 114, through a passage in the proximal end cap 110, and into the mesh portion 102. The distal end of the tether filament 116 can be tied into a knot 116A and/or can be fixed within the vascular plug 100 via adhesives. When the heater is activated, the tether filament 116 breaks, releasing the vascular plug 100 from the pusher 112.

The heater coil 114 is fixed at a distal end of the pusher 112 to a distal end of a core wire 124 that extends to a proximal end of the pusher 112. A first wire 118 is soldered to a distal end of the heater coil 114 at location 118A, and a second wire 120 is soldered to a proximal end of the heater coil 114 at location 120A, allowing power to be selectively supplied and thereby generate heat.

Figure 7:
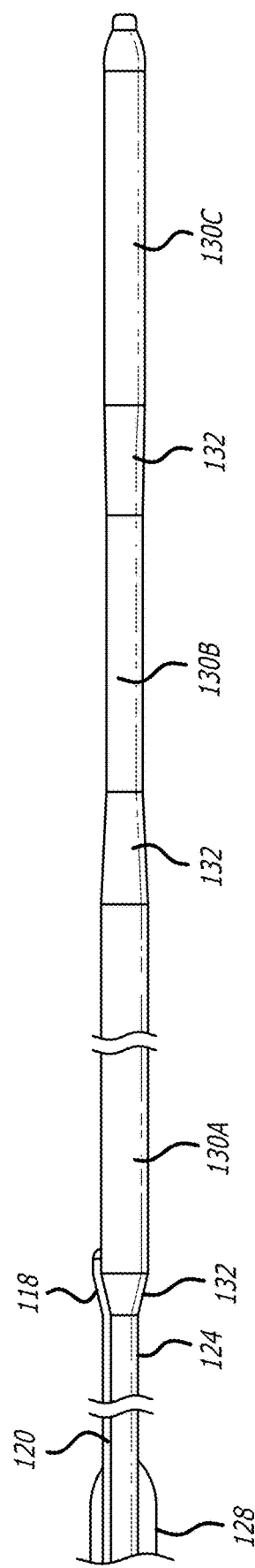
FIG. 7 illustrates a pusher and detachment mechanism.
Figure 8:
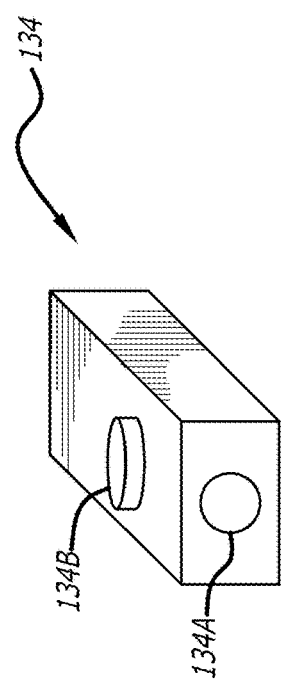
FIG. 8 illustrates a power supply and control system for the detachment mechanism.

The wires 118, 120 extend proximally within the outer tubular layers 126, 128 to the proximal end of the pusher 112; best seen in FIG. 7. The first wire 118 is fixed to a distal electrical contact 130 and the second wire 120 is connected to the core wires 124, which is ultimately connected to a middle electrical contact 130B. These contacts are further electrically isolated (e.g., with insulating spacers 132) to prevent an inadvertent short circuit. Hence, an electrically active circuit can be created by applying power to the distal electrical contact 130A and middle electrical contact 130B.

Power can be supplied to the contacts 130A and 130B by inserting the proximal end of the pusher 112 into passage 134A of a power control and supply unit 134. Preferably, the unit includes a button 1346 or similar user interface control to activate the power at a desired time. Optionally, the pusher 112 may include a proximal contact 130C that can be used by the unit 134 to determine if the pusher 112 has been properly seated in passage 134A. Similar detachment systems and/or variations can be found in U.S. Pat. No. 8,182,506, US20060200192, US20100268204, US20110301686, US20150289879, US20151073772, and US20150173773, all of which are incorporated by reference and can be used with this embodiment (as well as any others in this application).

In operation, the catheter 113, with the pusher 112 inside of it, is advanced within a vessel or lumen of a patient until the distal end of the catheter 112 is adjacent the target occlusion site. For example, the distal end of the catheter 113 may be positioned within or at the mouth of an aneurysm. Either prior to advancement or prior to insertion within the patient, the proximal end of the pusher 112, including the electrical contacts 130A, 1308, and 130C, are inserted into passage 134A of the supply unit 134.

Next, the pusher 112 is distally advanced (or optionally the catheter 113 is retracted) such that the vascular plug 100 is exposed at a distal end of the catheter 113 and located at the desired occlusion site (e.g., within an aneurysm or within a blood vessel). As the vascular plug 100 is exposed, the mesh portion 102 and the flexible membrane 104 expand, substantially blocking flow of bodily fluid (e.g., blood) past it.

Finally, the user activates the button 1346 to supply power through the pusher 112 and heater coil 114. As the heater coil 114 heats, it breaks the tether filament 116 that is connected to the vascular plug 100, thereby releasing the vascular plug 100 from the pusher 112. Finally, the pusher 112 can be withdrawn back into the catheter 113 and both devices can be withdrawn from the patient.

Alternately, the vascular plug 112 can be used in a temporary manner. Specifically, the vascular plug 100 can be deployed and then later withdrawn back into the catheter 113.

Figure 9:
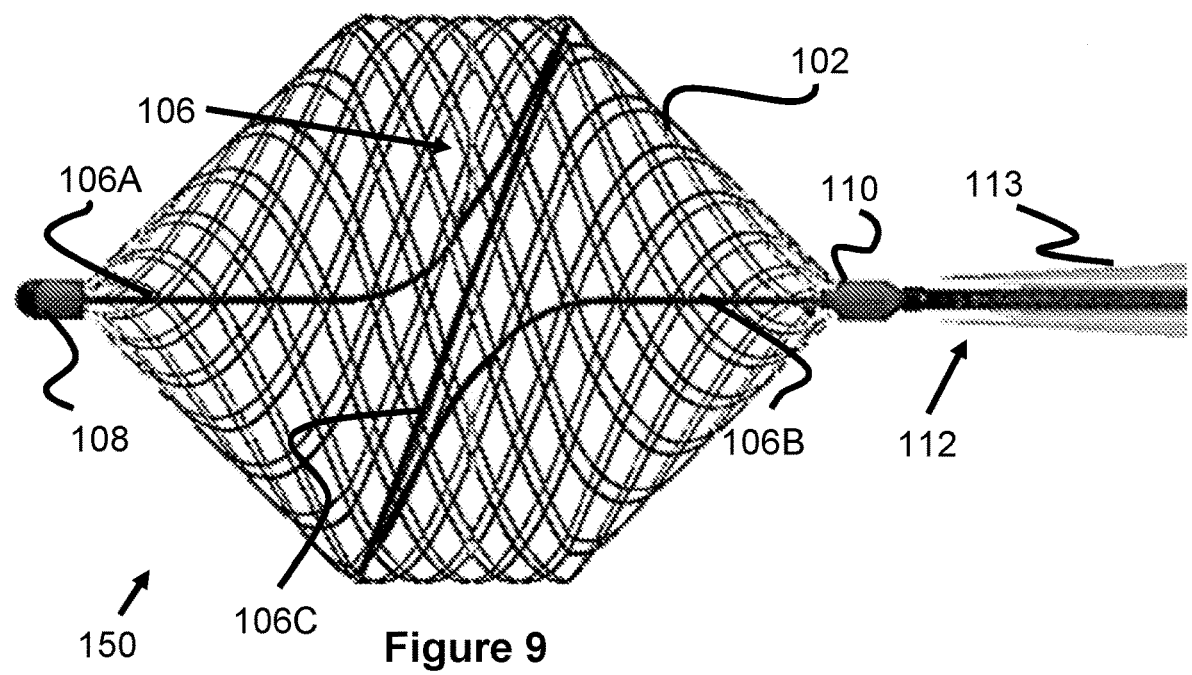
FIG. 9 illustrates another embodiment of a vascular plug.

FIG. 9 illustrates another embodiment of a vascular plug 150 that is generally similar to the previously described plug 100, but includes a ring portion 106C that positions the plane of the flexible membrane 104 at a non-perpendicular angle relative to the axis of the plug 150 and pusher 112. In one example, the plane of the ring portion 106C is angled at about 45 degrees relative to the axis of the pusher 112.

Figure 10:
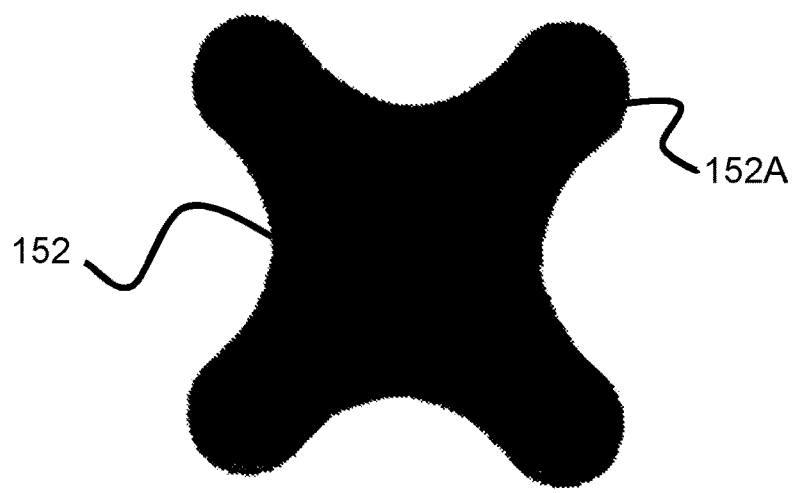
FIG. 10 illustrates an embodiment of a flexible membrane.
Figure 11:
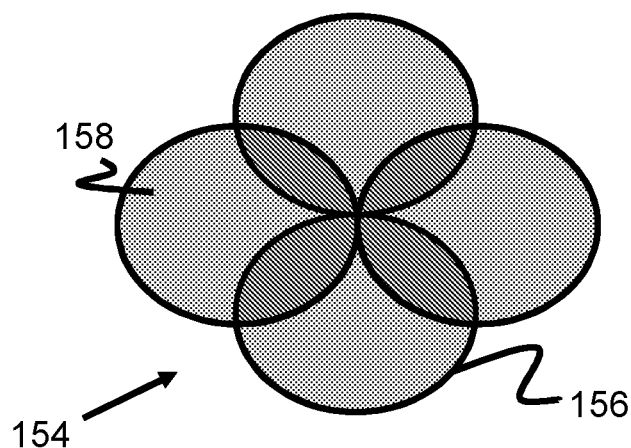
FIG. 11 illustrates an embodiment of a flexible membrane.

While the flexible membrane 104 forms a generally circular shape in vascular plug 100, other shapes are possible. For example, FIG. 10 illustrates a flexible membrane 152 having a generally "plus" shape with a plurality of radial arm portions 152. In another example, FIG. 11 illustrates a flexible membrane assembly 154 comprising a plurality of generally circular support rings 156 that each support discrete flexible membranes 158. The rings/membranes may partially overlap with each other and different numbers of rings/membranes may be used (e.g., 2, 3, 4, 5, or 6). Alternately, each support ring 156 may have a shape other than a circle, such as a square, triangular, wedge-shape, or oval.

Figure 12:
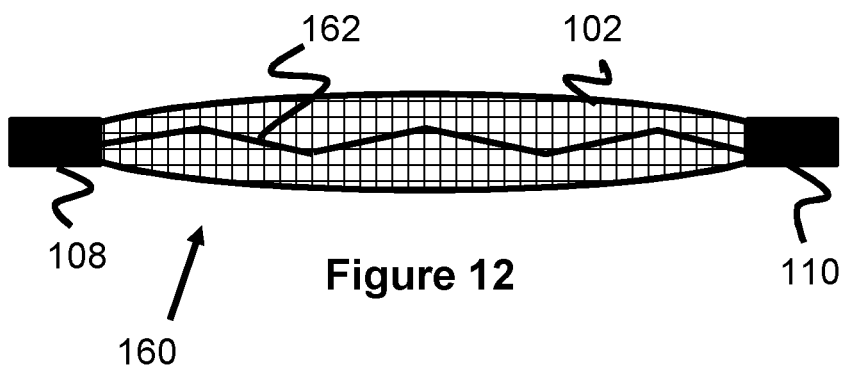
FIG. 12 illustrates a flexible plug with an elastic member within it.
Figure 13:
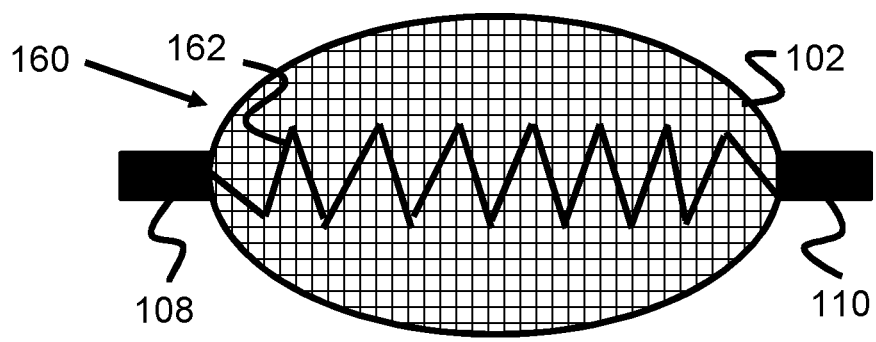
FIG. 13 illustrates a flexible plug with an elastic member within it.

Any of the embodiments of a vascular plug described in this specification can further include an elastic member 162 within the mesh portion 102 to assist in radial expansion. For example, FIG. 12 illustrates a vascular plug 160 (which may or may not have a flexible membrane 104) that has an elastic member 162 connected to the distal cap member 108 and proximal cap member 110. The vascular plug 160 is depicted in its compressed configuration (i.e., within the catheter 113), such that the elastic member 162 is stretched. In FIG. 13, the vascular plug 160 is released from the catheter 113, allowing the elastic member 162 to pull the cap members 108, 110 closer to each other, thereby expanding the mesh portion. The elastic member 162 can be any material that can provide elastic force, such as a spring or a stretchable, resilient polymer.

Figure 14:
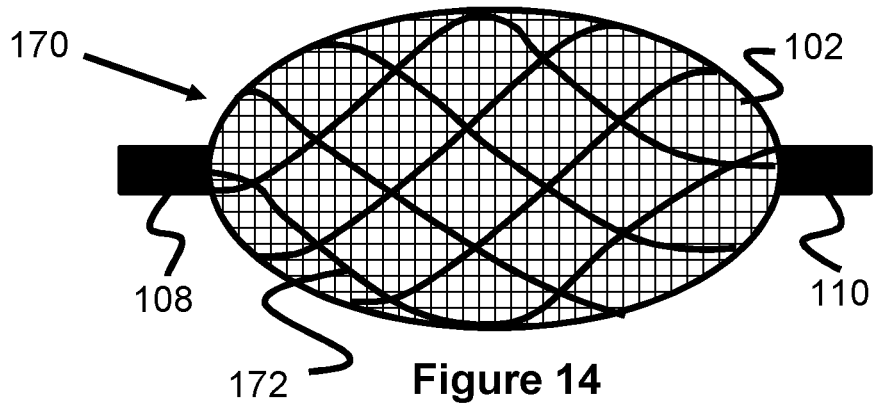
FIG. 14 illustrates another embodiment of a vascular plug.

Any of the mesh portions 102 described in this specification can further include strands of other material 172 woven into the mesh, such as PET fibers, hydrogel fibers, or PET-coated hydrogel fibers, as seen in the vascular plug 170 of FIG. 14. In one specific example, the mesh portion 102 is composed of 144 braided nitinol wires (8 wires are of 0.0025" diameter and 138 wires are of 0.001" diameter), with 20 PET threads adhered to a 0.004 inch stainless-steel wire that is sewn in an over-under pattern through the braided nitinol wires.

Figure 15:
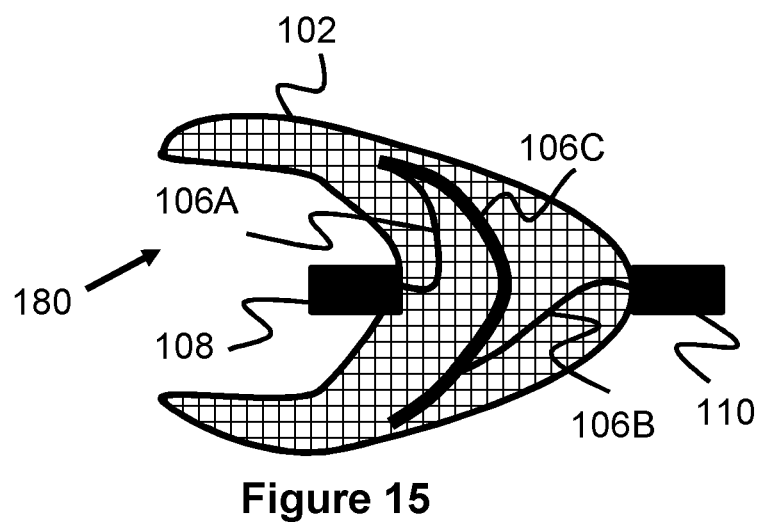
FIG. 15 illustrates another embodiment of a vascular plug.
Figure 16:
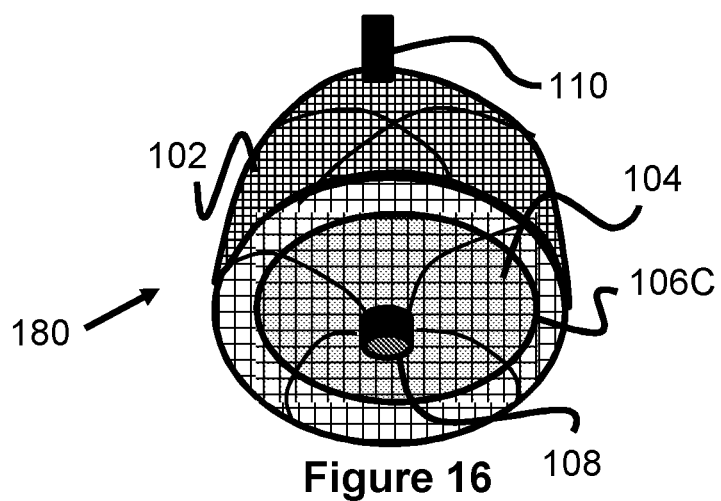
FIG. 16 illustrates another embodiment of a vascular plug.

It should be understood that the mesh portion 102 of any of the embodiments described in this specification can have expanded shapes other than the generally spherical shape of the vascular plug 100. For example, FIGS. 15 and 16 illustrates a cross sectional side view and a top perspective view, respectively, of a vascular plug 180 that expands to a "cup" or distally-facing concave shape. The support ring 106C and flexible membrane 104 are depicted as being within the interior of the mesh portion 102, but could alternately be positioned outside of the mesh portion 102, in the depression forming the distally-facing concave area.

Figure 17:
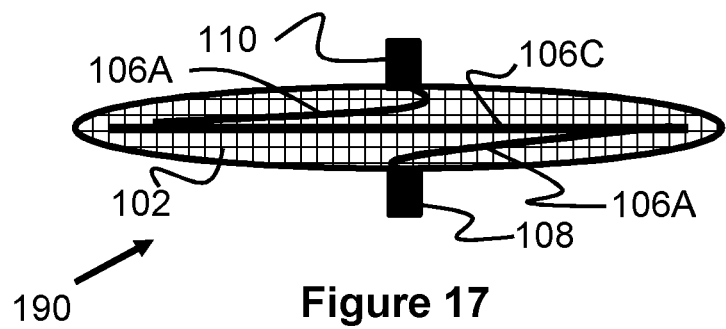
FIG. 17 illustrates another embodiment of a vascular plug.
Figure 18:
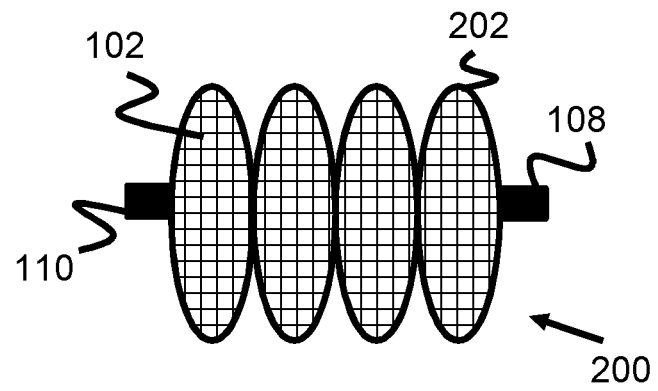
FIG. 18 illustrates another embodiment of a vascular plug.

In another example shown in FIG. 17, the mesh portion 102 of a vascular plug 190 can expand to a relatively flat or flattened oval shape. In yet another example shown in FIG. 18, a vascular plug 200 may expand to a plurality of axially-aligned bulb shapes 202 (e.g., 2, 3, 4, 5, 6), preferably heat-shaped as such from a single, continuous mesh portion 102. A flexible membrane 104 can be fixed within any of the bulbs 202, all of the bulbs 202, or any combination of the bulbs 202.

Figure 19:
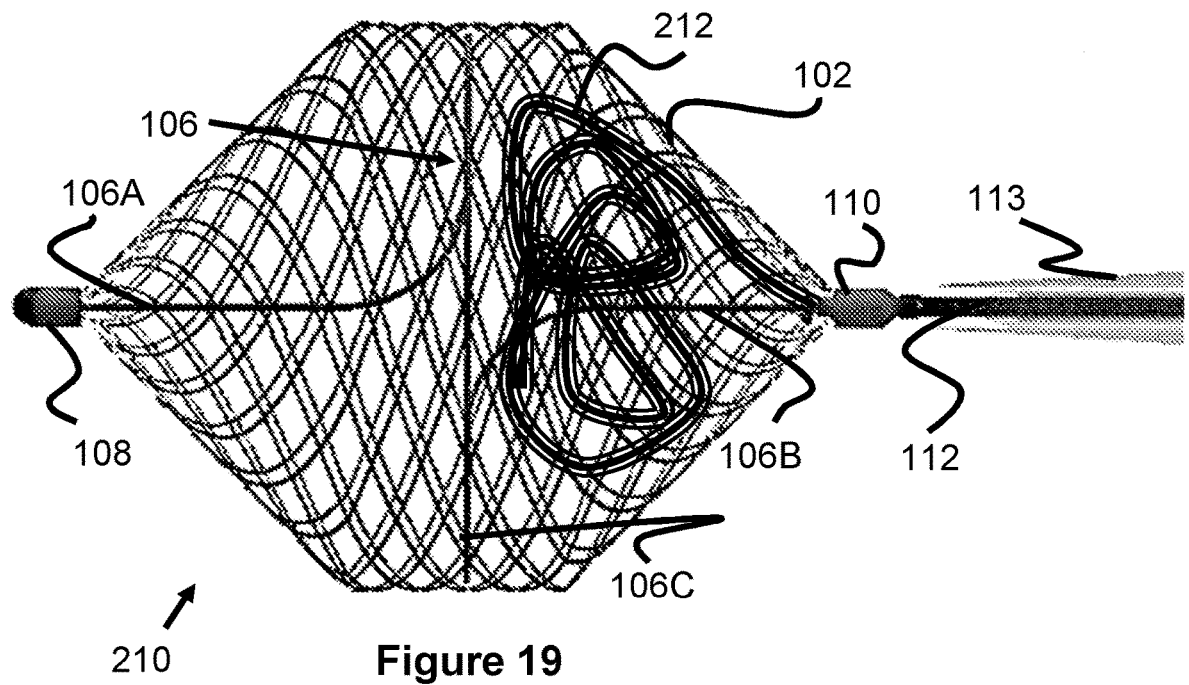
FIG. 19 illustrates embodiments of a vascular plug with microcoils.

Any of the embodiments disclosed in this specification can be further adapted to also deploy embolic microcoils 212 (or other embolic material, such a liquid embolic material or PET fibers) at various locations. For example, FIG. 19 illustrates an embodiment of a vascular plug 210 that is generally similar to previously described plug 100. However, the pusher 112 and proximal end cap 110 may include a passage within it that microcoils 212 can be pushed through into the proximal interior of the mesh portion 102 (the pusher 112 may be a catheter). The added microcoils 212 may further enhance blockage.

Figure 20:
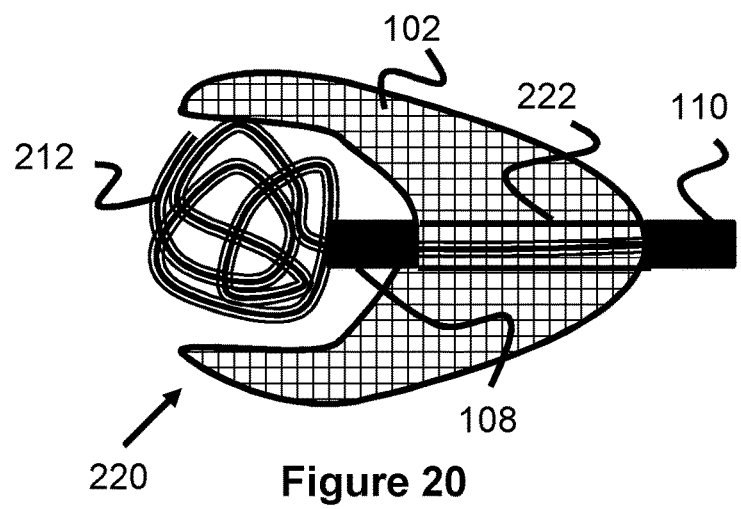
FIG. 20 illustrates embodiments of a vascular plug with microcoils.

In another example seen in FIG. 20, a vascular plug 220 can includes a passage 222 between the proximal cap member 110 to the distal cap member 108, allowing the microcoils 212 to be pushed to a distal side of the plug 220. In this example, the mesh portion 102 forms a distally facing concave shape, in which the microcoils 212 are positioned.

Figure 21:
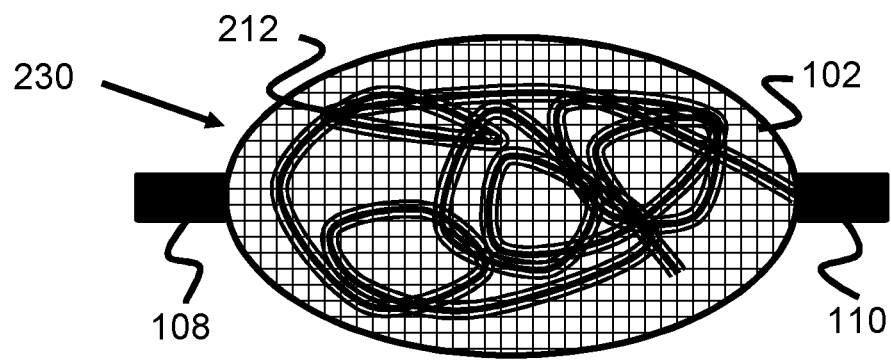
FIG. 21 illustrates another embodiment of a vascular plug.

In another example seen in FIG. 21, a vascular plug 230 lacks a flexible membrane 104, allowing the microcoil 212 to be pushed into the entire interior space of the mesh portion 102.

The microcoil 212 may have a three-dimensional secondary shape imparted to it, allowing it form curves, coils, and similar shapes when unconstrained. These secondary shapes are generally helpful for creating a frame around a treatment site, where smaller coils can subsequently be used to fill the treatment site. Other embodiments may utilize non-complex shaped embolic coils. In one example, the microcoil 212 has a primary wind diameter (this is the elongated shape of the coil when its constrained within a delivery catheter) that has a maximum value of about 0.023 inches, which allows use within a catheter (or a pusher 112 with a microcoil passage) of up to about 0.027 inches internal diameter. The secondary (delivered) wind size range may be between about 2 mm to about 20 mm. Optionally, the microcoil 212 may be coated or otherwise impregnated with hydrogel, and specifically pH-reactive hydrogel that expands upon contact with fluids with a particular pH (e.g., pH of blood).

Figure 22:
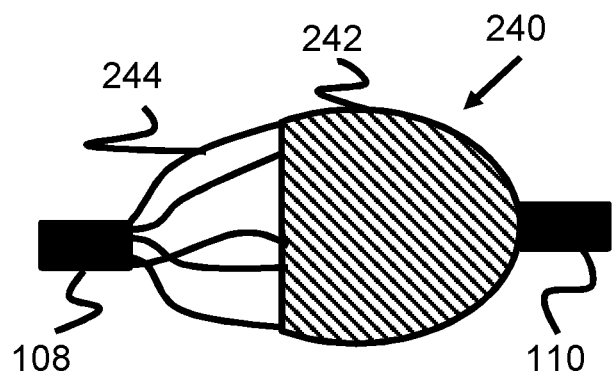
FIG. 22 illustrates another embodiment of a vascular plug with microcoils.

FIG. 22 illustrates another embodiment of a vascular plug 240, having a plurality of curved structural wires 244 extending between the proximal cap member 108 and the distal cap member 110. A flexible membrane 242 is connected over or beneath the structural wires 244 and can be composed of a thin-metallic film, such as those created via sputtering or vacuum deposition. Alternately, the flexible membrane 242 can be composed of mesh or a polymer, such as PET. Optionally, the vascular plug 244 is configured to deliver microcoils 212 within the interior of the flexible membrane.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A vascular plug for treating a patient, comprising:
   an elongated pusher;
   a mesh portion fixed to a distal end of the elongated pusher; the mesh portion having a radially compressed configuration when constrained in a catheter and a radially expanded configuration when unconstrained;
   a proximal support arm spanning a proximal section of an interior of the mesh portion, a distal support arm spanning a distal section of the interior of the mesh portion;
the proximal and distal support arms forming a ring portion in the interior of the mesh portion; and
   a membrane fixed to the ring portion, the membrane adopting a radially expanded configuration as the mesh portion adopts its radially expanded configuration, thereby limiting blood passage through the mesh portion.

2. The vascular plug of claim 1, further comprising a laminating layer disposed over the membrane.

3. The vascular plug of claim 2, wherein the membrane comprises PET and the laminating layer comprises ePTFE.

4. The vascular plug of claim 1, further comprising multiple proximal support arms and multiple distal support arms.

5. The vascular plug of claim 4, comprising two proximal support arms and two distal support arms.

6. The vascular plug of claim 1, wherein the ring portion expands to an orientation that is perpendicular to an axis between the proximal end and the distal end of the mesh portion.

7. The vascular plug of claim 1, wherein the ring portion expands within the interior of the mesh portion at a non-perpendicular angle relative to an axis of the elongated pusher.

8. The vascular plug of claim 1, wherein the membrane is connected to the ring portion via metal wires, polymer fibers, or adhesives.

9. The vascular plug of claim 1, wherein the membrane has a circular shape.

10. The vascular plug of claim 1, wherein the proximal support arm and the distal support arm curve radially outwardly near a center of the mesh portion to define the ring portion.

11. The vascular plug of claim 1, wherein the elongated pusher further comprises a tether attached to the mesh portion and a heater coil configured to break the tether to release the mesh portion.

12. The vascular plug of claim 1, wherein the elongated pusher further comprises a microcoil that is distally advanceable into the interior of the mesh portion.

13. The vascular plug of claim 1, wherein the membrane expands to an orientation that is perpendicular to an axis between the proximal end and the distal end of the mesh portion.

14. The vascular plug of claim 1, wherein the membrane expands within the interior of the mesh portion at a non-perpendicular angle relative to an axis of the elongated pusher.

15. A vascular plug for treating a patient, comprising:
   an elongated pusher;
   a mesh portion fixed to a distal end of the elongated pusher; the mesh portion having a radially compressed configuration when constrained in a catheter and a radially expanded configuration when unconstrained;
   a proximal support arm spanning a proximal section of the interior of the mesh portion and a distal support arm spanning the distal section of the interior of the mesh portion; the proximal and distal support arms forming a ring portion in an interior of the mesh portion, where the portion ring expands within the interior of the mesh portion at a non-perpendicular angle relative to an axis of the elongated pusher; and
   a membrane fixed to the ring portion, the membrane adopting a radially expanded configuration as the mesh portion adopts its radially expanded configuration, thereby limiting blood passage through the mesh portion.

16. The vascular plug of claim 15 wherein the proximal support arm and the distal support arm curve radially outwardly near a center of the mesh portion to define the ring portion.

17. A vascular plug for treating a patient, comprising:
   an elongated pusher;
   a mesh portion fixed to a distal end of the elongated pusher; the mesh portion having a radially compressed configuration when constrained in a catheter and a radially expanded configuration when unconstrained;
   a proximal support arm spanning a proximal section of the interior of the mesh portion and a distal support arm spanning the distal section of the interior of the mesh portion; the proximal and distal support arms forming a ring portion in the interior of the mesh portion; and
   a membrane fixed to the ring portion, the membrane adopting a radially expanded configuration at a non-perpendicular angle relative to an axis of the elongated pusher as the mesh portion adopts its radially expanded configuration, thereby limiting blood passage through the mesh portion.

18. The vascular plug of claim 17, further comprising two proximal support arms and two distal support arms.

* * * * *